United States Patent [19]

Davis

[11] Patent Number: 5,108,974
[45] Date of Patent: Apr. 28, 1992

[54] PREPARATION OF VANADIUM-PHOSOPHORUS-OXIDE CATALYST PRECURSOR

[75] Inventor: Gershon J. Davis, White Plains, N.Y.

[73] Assignee: Akzo N.V., Arnhem, Netherlands

[21] Appl. No.: 630,128

[22] Filed: Dec. 19, 1990

[51] Int. Cl.$^5$ .................. B01J 27/198; C01B 15/16; C07D 37/34
[52] U.S. Cl. .................. 502/209; 423/307; 549/259
[58] Field of Search ............ 502/209; 423/307

[56] References Cited

U.S. PATENT DOCUMENTS

| | | | |
|---|---|---|---|
| 4,062,873 | 12/1977 | Harrison | 502/209 |
| 4,064,070 | 12/1977 | Harrison | 502/209 |
| 4,382,876 | 5/1983 | Neubold et al. | 502/209 |
| 4,632,916 | 12/1986 | Bither, Jr. | 520/209 |
| 4,677,084 | 6/1987 | Bergna | 502/8 |

*Primary Examiner*—Paul E. Konopka
*Attorney, Agent, or Firm*—Richard P. Fennelly; Louis A. Morris

[57] ABSTRACT

Vanadium pentoxide can be reduced to the +4 oxidation state from the +5 state, in the manufacture of vanadium-phosphorus-oxide catalyst precursor, $(VO)_2H_4P_2O_9$, by using phosphoric acid as the reducing agent rather than benzyl alcohol. Use of an alkyl silicate with the phosphoric acid insures the correct crystalline species, $(VO)_2H_4P_2O_9$, as indicated by X-ray diffraction.

4 Claims, No Drawings

PREPARATION OF VANADIUM-PHOSOPHORUS-OXIDE CATALYST PRECURSOR

BACKGROUND OF THE INVENTION

It is well known in the art to synthesize vanadium-phosphorus-oxide (VPO) catalysts for the selective oxidation of $C_4$ hydrocarbons to maleic anhydride. A recent article which affords an overview of this area of technology is H. S. Horowitz et al., Applied Catalysis, 38 (1988) 193-210 and U.S. Pat. No. 4,677,084 to H. E. Bergna which are each incorporated herein in their entirety.

The VPO catalyst precursor is ordinarily prepared by reducing vanadium pentoxide to vanadium tetraoxide with benzyl alcohol in an isobutanol solution. The benzyl alcohol is oxidized to benzaldehyde. The vanadium tetraoxide is then reacted with phosphoric acid in the presence of tetraethylorthosilicate to form the desired precursor phase having the formula $(VO)_2H_4P_2O_9$. U.S. Pat. No. 4,632,916, at Col. 4, lines 1-6 indicates that various reductants can be employed including isobutanol, benzyl alcohol, and "reduced acids of phosphorus like $H_3PO_3$. In the case of using isobutanol and benzyl alcohol, the isobutanol is oxidized more slowly to isobutyraldehyde, and butyral.

SUMMARY OF THE INVENTION

The foregoing procedure can be varied without using benzyl alcohol as the reductant if the vanadium pentoxide is reduced to the desired vanadium tetraoxide by being heated in the presence of a mixture of an alcohol and sufficient phosphoric acid. Even though the reduction of the pentoxide to the tetraoxide is achieved, the catalyst precursor that is precipitated in this system will not be crystalline $(VO)_2H_4P_2O_9$ unless an alkyl silicate is present. When this specific compound is formed, rather than mixed vanadium phosphates, catalysts made from it give butane to maleic anhydride yields of up to about 90%, rather than 50% to 60%.

DETAILED DESCRIPTION OF THE INVENTION

The reduction of the vanadium pentoxide is accomplished in accordance with the instant invention by heating the pentoxide in an appropriate solvent such as an alcohol, e.g., isobutanol, in the presence of a mixture of tetraethylorthosilicate and phosphoric acid. The vanadium pentoxide is preferably in milled form, and the amount of phosphoric acid used should be sufficient (when taken with the later added amount of phosphoric) to give a P/V ratio in the final catalyst of from about 0.9:1 to about 1.3:1.0 as mentioned at Col. 4, lines 21-33, of U.S. Pat. No. 4,632,916. The mixture of vanadium pentoxide, solvent, phosphoric acid, and tetraethylorthosilicate is preferably heated to reflux to achieve the desired degree of reduction.

Then, additional phosphoric acid is added (to achieve the above-stated P/V ratio in the final catalyst) followed by additional refluxing to precipitate the desired crystalline $(VO)_2H_4P_2O_9$ catalyst precursor for a vanadium-phosphorus mixed oxide catalyst.

The Examples which follow set forth in more detail a various embodiments of the claimed invention.

EXAMPLE 1

Approximately 7 lbs of $V_2O_5$ were finely ground through a model JT-6 Fitz mill using a 325 mesh screen with a canvass sock. The milling took place over a period of approximately 15 minutes and the $V_2O_5$ was fed slowly with dry ice.

A 5 liter flask equipped with a heating mantle with variac, stirrer, and reflux condenser was charged with the following ingredients:

| Ingredient | Weight (grams) |
| --- | --- |
| Isobutanol | 2004 |
| $V_2O_5$ (air-dried) | 250 |
| Tetraethylorthosilicate | 305 |
| Phosphoric Acid (85%) | 160 |

The resulting mixture was heated to reflux (about 100C) for approximately 13 hours. Then, the remainder of the 85% phosphoric acid (206 gm) was added. The resulting mixture was refluxed for 6-7 hours with a blue-green precipitate forming during this step.

The resulting reaction mixture was cooled down to close to room temperature and filtered through a 10-15 micron fritted glass filter with vacuum. The product retained by the filter was washed twice with 250 ml of isobutanol and was dried in an oven at 145C and vacuum (20 mm Hg) for eight hours. The product weighed about 490 gm and it was passed through a 100 mesh screen to form a more uniform particle size. The product was confirmed by X-ray diffraction to be a $(VO)_2H_4P_2O_9$ catalyst precursor for a vanadium-phosphorus mixed oxide catalyst. The X-ray diffraction peaks for $(VO)_2H_4P_2O_9$ and their relative intensity (100 = the height of the most intense peak) were:

| $2\theta$ | Rel. Intensity |
| --- | --- |
| 30.347 | 100 |
| 15.481 | 68 |
| 26.998 | 60 |
| 19.604 | 43 |
| 24.098 | 38 |
| 28.736 | 26 |
| 31.982 | 23 |
| 33.667 | 21 |
| 14.940 | 19 |
| 33.409 | 15 |
| 37.328 | 15 |
| 34.142 | 14 |
| 39.912 | 9 |
| 37.136 | 7 |
| 36.775 | 7 |
| 35.022 | 6 |
| 37.637 | 6 |
| 34.784 | 5 |
| 36.403 | 5 |
| 39.620 | 4 |

EXAMPLES 2-21

A series of variations were made in the procedure of Example 1 where certain reagents were either present or absent or were changed in some manner. The X-ray diffraction pattern of the resulting product either conformed to that of $(VO)_2H_4P_2O_9$ ("OK") or did not ("NG").

| i-butanol 500 ml | benzyl alcohol (50 ml) | TEOS (61 g) | V₂O₅ (50 g) | H₃PO₄ (85%) 75 g | XRD Data |
|---|---|---|---|---|---|
| Yes | Yes | Yes | Yes | Yes | OK |
| Yes | No | Yes | Yes | NH₄CO₃ | NG |
| Yes | No | Yes | Yes | 1 gm | OK |
| Yes | Yes | Yes | 200 gm | Yes | OK |
| Yes | Yes | Yes | Yes | Yes | OK |
| Yes | Yes | Yes | Yes | Yes | OK |
| Yes | Yes | Yes | Yes | Yes | OK |
| Yes | No | Yes | Yes | Yes | OK |
| Yes | Yes | Yes | Yes | Yes | OK |
| Yes | No | Yes | Yes | Yes | OK |
| Yes | No | No | Yes | 100% | NG |
| Yes | Yes | No | Yes | 100% | NG |
| 2500 ml | 250 ml | 305 ml | 250 ml | 375 g | OK |
| 2500 ml | No | 305 ml | 250 ml | 375 g | OK |
| Yes | No | No | Yes | 100% | NG |
| Yes | No | ethanol | Yes | 100% | NG |
| Yes | Yes | No | Yes | 100% | NG |
| Yes | No | Yes | Yes | Yes | OK |
| Yes | Yes | Yes | Yes | Yes | OK |
| Yes | No | Yes | Yes | Yes | OK |

I claim:

1. A process for forming the vanadium-phosphorus-oxide catalyst precursor $(VO)_2H_4P_2O_9$ which comprises reducing milled $V_2O_5$ to $V_2O_4$ by heating the $V_2O_5$ in the presence of an alcohol, an alkyl silicate, and phosphoric acid and precipitating the product with additional phosphoric acid in the presence of the alkyl silicate.

2. A process as claimed in claim 1 wherein at least about 80% of the milled $V_2O_5$ is less than 325 mesh.

3. A process as claimed in claim 1 wherein the alkyl silicate is ethyl silicate.

4. A process as claimed in claim 1 wherein at least 80% of the milled $V_2O_5$ is less than 325 mesh and the alkyl silicate is ethyl silicate.

* * * * *